United States Patent
Cuesta Valentin et al.

(10) Patent No.: US 11,241,192 B2
(45) Date of Patent: Feb. 8, 2022

(54) SYSTEM AND METHOD FOR PREDICTING THE VIABILITY OF A BODY TISSUE IN A PATIENT, AND MEASURING DEVICE USED THEREIN

(75) Inventors: Miguel Angel Cuesta Valentin, Amsterdam (NL); Alexander Arnold Frederik Adriaan Veenhof, Amsterdam (NL)

(73) Assignee: Veenhof Medical Devices B.V., Maastricht (NL)

( * ) Notice: Subject to any disclaimer, the term of this patent is extended or adjusted under 35 U.S.C. 154(b) by 1072 days.

(21) Appl. No.: 14/130,478

(22) PCT Filed: Jul. 4, 2012

(86) PCT No.: PCT/NL2012/050472
§ 371 (c)(1),
(2), (4) Date: Dec. 31, 2013

(87) PCT Pub. No.: WO2013/006053
PCT Pub. Date: Jan. 10, 2013

(65) Prior Publication Data
US 2014/0135604 A1    May 15, 2014

Related U.S. Application Data

(60) Provisional application No. 61/504,255, filed on Jul. 4, 2011.

(30) Foreign Application Priority Data

Jul. 4, 2011 (NL) ...................................... 2007038

(51) Int. Cl.
*A61B 5/00* (2006.01)
*A61B 5/026* (2006.01)
(Continued)

(52) U.S. Cl.
CPC .......... *A61B 5/4848* (2013.01); *A61B 5/0053* (2013.01); *A61B 5/0205* (2013.01);
(Continued)

(58) Field of Classification Search
CPC combination set(s) only.
See application file for complete search history.

(56) References Cited

U.S. PATENT DOCUMENTS 3,610,233 A * 10/1971 Barkalow ............ A61H 31/006
601/106
5,579,763 A    12/1996 Weil
(Continued)

FOREIGN PATENT DOCUMENTS

JP    11-501827 A    2/1999
JP    2005-052665 A    3/2005
(Continued)

OTHER PUBLICATIONS

Fischer M, et al., "Simultaneous measurement of digital artery and skin perfusion pressure by the laser Doppler technique in healthy controls and patients with peripheral arterial occlusive disease.", Eur J Vasc Endovasc Surg. Aug. 1995; 10(2):231-6 (Fisher).*
(Continued)

*Primary Examiner* — Christian Jang
*Assistant Examiner* — Mitchell E Alter
(74) *Attorney, Agent, or Firm* — Steven M. Koehler; Westman, Champlin & Koehler, P.A.

(57) ABSTRACT

The invention relates to a system for predicting the viability of a body tissue in a patient. The system comprises a computing device, and a first pressure measuring device for measuring local perfusion pressure in the body tissue of the patient. This measuring device is connected to the computing device. A second pressure measuring device is provided for measuring the systemic perfusion pressure of the patient,
(Continued)

said second pressure measuring device being connected to the computing device. A feedback indicator is connected to the computing device and is adapted to indicate the viability of the tissue calculated by the computing device on the basis of the measured local and systemic perfusion pressures. The invention also includes a method of predicting the viability of the body tissue and to the first pressure measuring device.

23 Claims, 4 Drawing Sheets

(51) Int. Cl.

| | | |
|---|---|---|
| *A61B 5/0205* | (2006.01) | |
| *A61B 5/0215* | (2006.01) | |
| *A61B 5/022* | (2006.01) | |
| *A61B 5/1455* | (2006.01) | |

(52) U.S. Cl.
CPC ............ *A61B 5/026* (2013.01); *A61B 5/0215* (2013.01); *A61B 5/0261* (2013.01); *A61B 5/02233* (2013.01); *A61B 5/14551* (2013.01); *A61B 5/42* (2013.01)

(56) References Cited

U.S. PATENT DOCUMENTS

| | | | | |
|---|---|---|---|---|
| 5,722,419 A * | 3/1998 | Semmlow | ............ | A61B 5/04884 600/546 |
| 5,876,357 A * | 3/1999 | Tomer | ................... | A61B 5/1076 600/591 |
| 7,618,376 B2 | 11/2009 | Kimball | | |
| 8,118,206 B2 | 2/2012 | Zand | | |
| 9,204,830 B2 | 12/2015 | Zand et al. | | |
| 2004/0006263 A1 | 1/2004 | Anderson | | |
| 2004/0127800 A1* | 7/2004 | Kimball | ............... | A61B 5/0261 600/483 |
| 2006/0020179 A1 | 1/2006 | Anderson | | |
| 2006/0149154 A1* | 7/2006 | Stephens | ................ | A61B 5/445 600/504 |
| 2008/0071155 A1* | 3/2008 | Kiani | ................. | A61B 5/02416 600/324 |
| 2008/0183059 A1* | 7/2008 | LaPlante | ............ | A61B 5/02007 600/363 |
| 2009/0234248 A1* | 9/2009 | Zand | .................... | A61B 5/0031 600/587 |
| 2011/0152646 A1 | 6/2011 | Anderson | | |
| 2011/0224518 A1* | 9/2011 | Tindi | ................. | A61B 5/14552 600/323 |
| 2012/0273548 A1* | 11/2012 | Ma | ................... | A61B 17/06166 227/176.1 |

FOREIGN PATENT DOCUMENTS

| | | |
|---|---|---|
| JP | 2005052665 | 3/2005 |
| JP | 2005-528156 A | 9/2005 |
| JP | 2007-525253 A | 9/2007 |
| JP | 2007525253 | 9/2007 |
| WO | 96/25087 | 8/1996 |
| WO | 96/25087 A1 | 8/1996 |
| WO | 03/101277 | 12/2003 |
| WO | 2005/030038 | 4/2005 |
| WO | 2005/030038 A2 | 4/2005 |
| WO | 2006113394 | 10/2006 |
| WO | 2007008057 | 1/2007 |
| WO | 2009115992 | 9/2009 |
| WO | 2013006053 A1 | 1/2013 |

OTHER PUBLICATIONS

Lima, Alexandre Pinto, Peter Beelen, and Jan Bakker. "Use of a peripheral perfusion index derived from the pulse oximetry signal as a noninvasive indicator of perfusion." Critical care medicine 30.6 (2002): 1210-1213.*
Search Report and Written Opinion from corresponding PCT/NL2012/050472 dated Oct. 11, 2012.
Linas Urbanavicius: "How to assess intestinal viability during surgery: A review of techniques", World Journal of Gastrointestinal Surgery, vol. 3, No. 5, Jan. 1, 2011.
Copy of Japanese Office Action for Japanese patent application No. 2014-518849, dated May 17, 2016.
Esophageal PCO2 as a monitor of perfusion failure during hemorrhagic shock, Sato et al., (1997).
Systemic perfusion pressure and blood flow before and after administration of epinephrine during experimental cardiopulmonary resuscitation, Rubertsson et al.
Decision of Rejection from Japanese Patent Application No. 2014-518849, dated Apr. 3, 2017.
Notice of Reasons for Rejection as received from the Japanese Patent Office for Japanese Patent Application No. 2017-150722, dated Jun. 4, 2018, with English translation.
Dr. Manish Bhatia, "Homeopathic medicines for Surgical Shock, Postoperative Shock", Aug. 31, 2009, https://hpathy.com/cause-symptoms-treatment/surgical-shock-postoperative-shock/.

* cited by examiner

SYSTEM AND METHOD FOR PREDICTING THE VIABILITY OF A BODY TISSUE IN A PATIENT, AND MEASURING DEVICE USED THEREIN

CROSS-REFERENCE TO RELATED APPLICATION

The present application is a national stage filing of International patent application Serial No. PCT/NL2012/050472, filed Jul. 4, 2012, and published as WO 2013/006053 A1 in English.

BACKGROUND

The discussion below is merely provided for general background information and is not intended to be used as an aid in determining the scope of the claimed subject matter. Aspects of the invention relate to a system and method for predicting the viability of a body tissue in a patient, particularly for use in anastomotic surgery.

After colorectal surgery, in many patients a new connection between two healthy bowel segments is made, the so-called anastomosis. Anastomotic leakage remains a serious complication following colorectal surgery and its reported prevalence varies widely from 1% to 39%. Not only may this complication result in an acute life-threatening condition, cancer patients show a higher local reoccurrence rate following anastomotic complications with local abscess formation. Anastomotic complications are thought to be related to inadequate perfusion of the anastomosis. Currently, viability of the bowel, before performing the anastomosis, is estimated by the color of the tissue. This remains very subjective and based on the experience of the surgeon.

Several publications regarding other methods for evaluating bowel viability have recently been reported, such as perfusion by the Laser Doppler Flowmetry (LDF) and oxygenation by the Near-infrared Spectroscopy (NIRS). However, in these publications the perfusion at the site of the anastomosis is measured in an abstract value which can not be compared to the systemic perfusion of the body at the time of surgery.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

In a first aspect, the invention provides a system for predicting the viability of a body tissue in a patient, comprising:

a computing device, a first pressure measuring device for measuring local perfusion pressure in the body tissue of the patient, said measuring device being connected to the computing device, a second pressure measuring device for measuring the systemic perfusion pressure of the patient, said perfusion pressure meter being connected to the computing device, a display connected to the computing device and adapted to show an index on the basis of the local and systemic perfusion pressures calculated by the computing device, said index being indicative for the viability of the tissue.

A method of predicting the viability of a tissue in a patient comprises the steps of:

measuring the local perfusion pressure in a body tissue of a patient, measuring the systemic perfusion pressure of the patient, feeding the measured values of the perfusion pressures to a computing device, which registers it and calculates an index on the basis of the local and systemic perfusion pressure values, displaying the index on the basis of the local and systemic perfusion pressures, said index being indicative for the viability of the tissue.

By measuring both the local perfusion pressure and the systemic perfusion pressure it is possible to obtain a patient independent index on the basis of which the surgeon can reliably predict tissue viability and therefore be able to take appropriate measures, such as removing the non-viable tissue, to prevent to a large extent anastomotic leakage after surgery.

In one embodiment the first pressure measuring device comprises a clamp having two clamping members for clamping the tissue there between, a pressing unit for applying pressure on at least one of the clamping members, and a pressure meter for measuring the pressure applied by the pressing unit. Particularly, it may also comprise a perfusion sensor for measuring the perfusion in the tissue at least near the clamp.

The clamp enables to exert a pressure onto the tissue that influences the perfusion therein. This perfusion can be measured by means of a perfusion sensor, such as a Laser-Doppler sensor or other available sensors. The relationship between applied pressure and perfusion can be registered, and it is for example possible to register the pressure at which the perfusion stops, or at which reperfusion starts. These values may be used as an input in the computing device and the index can be calculated on the basis of one of these values and the value of the systemic perfusion pressure which is measured substantially simultaneously.

The perfusion sensor may be positioned in one of the clamping members so that perfusion can be measure right at the spot where pressure is exerted, but it would also be possible to measure perfusion just downstream of the pressure spot.

In a simple embodiment, the pressing unit is a pneumatic pressing unit including a pump. A pneumatic pressing unit is accurate, able to maintain a pressure constant and allows an easy measurement of the pressure. Then, the pressure meter may be a manometer, e.g. integrated in the pump. This is a device that is easy to use and already used in operating rooms.

If the computing device also includes a controller, for controlling the pump and pressure measuring devices, the measurements may be done automatically, which makes the measurements easier and more reliable.

The second pressure measuring device may be an arterial line with which the systemic perfusion pressure can be measured continuously. Such device is available in most operating rooms.

An aspect of the invention also includes a measuring device for measuring the local perfusion pressure in a body tissue of a patient, comprising:

a clamp having two clamping members for clamping the tissue there between, a pressing unit for applying pressure on at least one of the clamping members, a pressure meter for measuring the pressure applied by the pressing unit, and a perfusion sensor for measuring the perfusion in the tissue at least near the clamp.

BRIEF DESCRIPTION OF THE DRAWINGS

Further details and advantages of the invention follow from the description below with reference to the drawing showing an embodiment of the invention by way of example.

DETAILED DESCRIPTION OF THE ILLUSTRATIVE EMBODIMENTS

Figure 1:
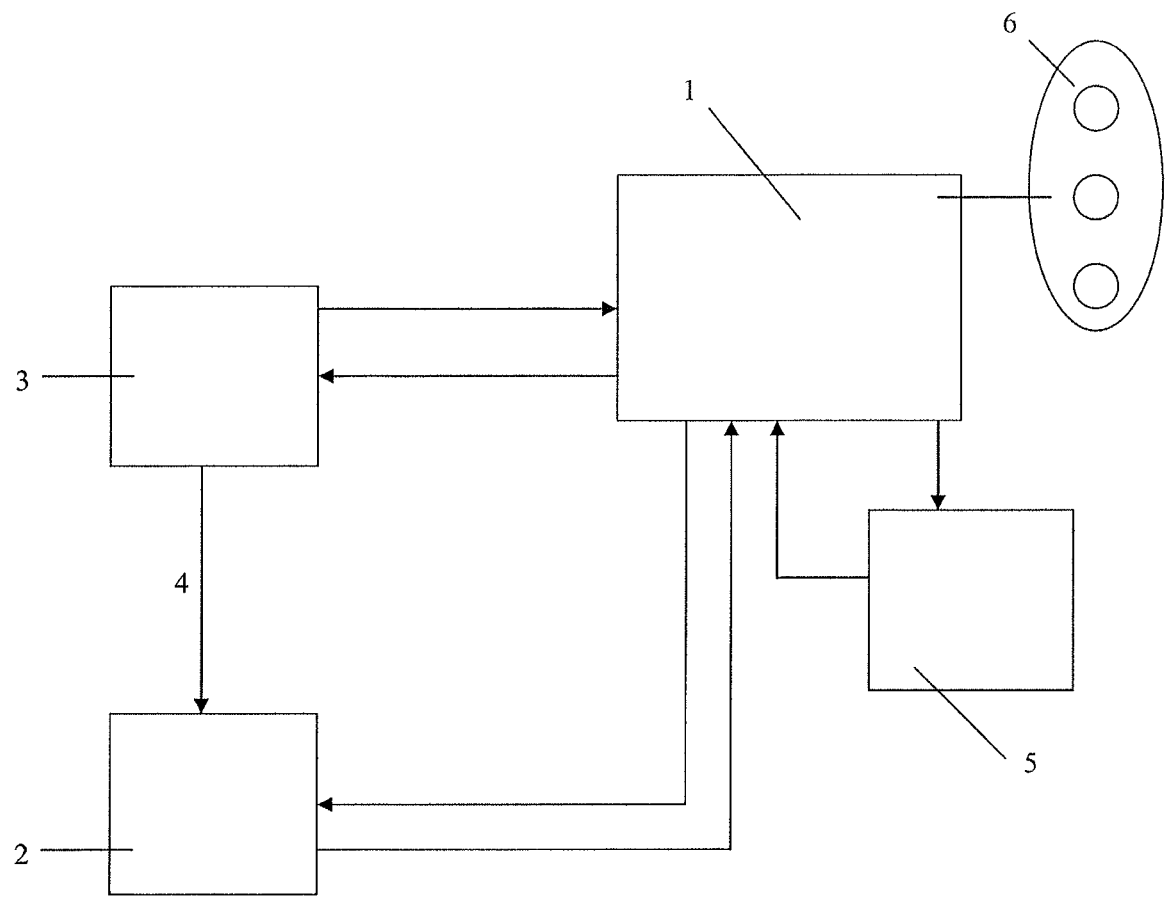
FIG. 1 is a scheme of a system for predicting the viability of a body tissue in a patient.

FIG. 1 shows a system for predicting the viability of a body tissue in a patient. This body tissue is for example part of a body organ, like the bowel, large and small intestine, oesophagus, stomach, rectum and the like. The viability is normally determined during surgery (open surgery or laparoscopy), especially if tissue is removed and adjacent tissue parts must be connected to each other, such as through anastomosis. In order to predict whether there is a considerable risk that the anastomosis is going to leak, the viability of the tissue parts to be connected should be determined. More tissue should for example be removed if tissue to be connected is not sufficiently viable.

The system includes a computing device 1 which is used to control the system and is able to process measured values and compute on the basis thereof the viability of the tissue to be evaluated.

There is a first pressure measuring device 2 for measuring local perfusion pressure in the body tissue of the patient. The measuring device 2 is connected to the computing device 1, in order to send measuring signals to the computing device, and possibly also to receive any control signals. The first pressure measuring device 2 will be discussed in further detail later on.

A pressing unit, e.g. a pump 3 is connected through a pressure line 4 to the measuring device 1 and to the computing device to receive control signals from and to send measuring value signals to the computing device 1. The pump 3 is a means to pressurize the measuring device 2 in order to determine the local perfusion pressure in the tissue. The pump may be pneumatic or hydraulic, but the pump may also be replaced by another pressing unit, such as a mechanic member like a screw. The pressing unit may be integrated with the measuring device 2 or may be separate from it. If the pressing unit is pneumatic or hydraulic, the exerted pressure can be determined by a manometer as a pressure meter which might be integrated in the pump. In case of a mechanic pressing unit the pressure meter can be a strain gauge, load cell, spring suspension or the like.

The system further includes a second pressure measuring device 5 for measuring the systemic perfusion pressure of the patient. The perfusion pressure measuring device or pressure meter 5 is connected to the computing device 1 to receive control signals and to send measuring value signals thereto. The pressure meter 5 may for example be a pneumatic blood pressure meter (in the form of a belt) to measure blood pressure intermittently or an arterial line or other device to measure the blood pressure continuously/real time. The systemic pressure may be measured in the arm (wrist, elbow), or in other parts of the body where the systemic pressure can be measured, such as the groin. The arterial line may already be there on behalf of the surgery, so that no additional equipment is required. It is also possible that the system includes a means to communicate with a second pressure measuring device already present in the surgery room, such as a wireless communication means, for example Bluetooth and the like.

A display 6 is connected to the computing device 1 as a visual feedback indicator adapted to indicate the viability of the tissue calculated by the computing device on the basis of the measured local and systemic perfusion pressures. The display may show an indicative index calculated on the basis of the pressures, for example the ratio between both pressures, but it may also be a traffic light showing colors like green, orange and red as an indication of the viability of the tissue. Other feedback indicators are conceivable, such as auditory feedback indicators and the like.

The method used for predicting the viability of a tissue in a patient may include the following steps:

measuring the local perfusion pressure in a body tissue of a patient by means of the first pressure measuring device 2, measuring the systemic perfusion pressure of the patient by the second pressure measuring device 5, either simultaneously or with some allowable time shift (for example 1 minute), feeding the measured values of the perfusion pressures to the computing device 1, which registers it and calculates an index on the basis of the local and systemic perfusion pressure values, and providing feedback through the display 6 on the basis of the index which is indicative for the viability of the tissue.

Figure 2:
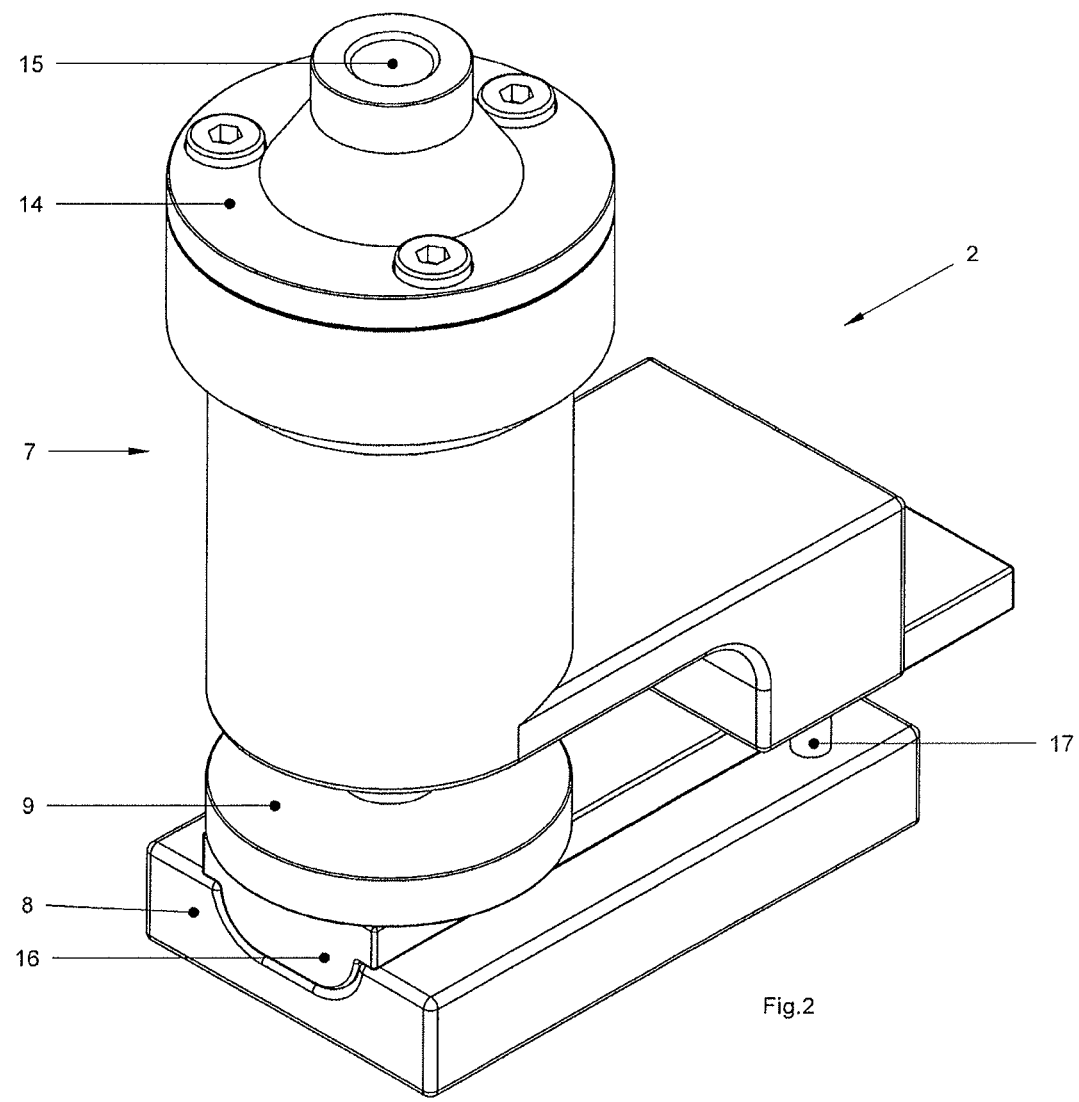
FIG. 2 is a schematic perspective view of a measuring device for measuring local perfusion pressure which may be used in the system of FIG. 1.
Figure 3:
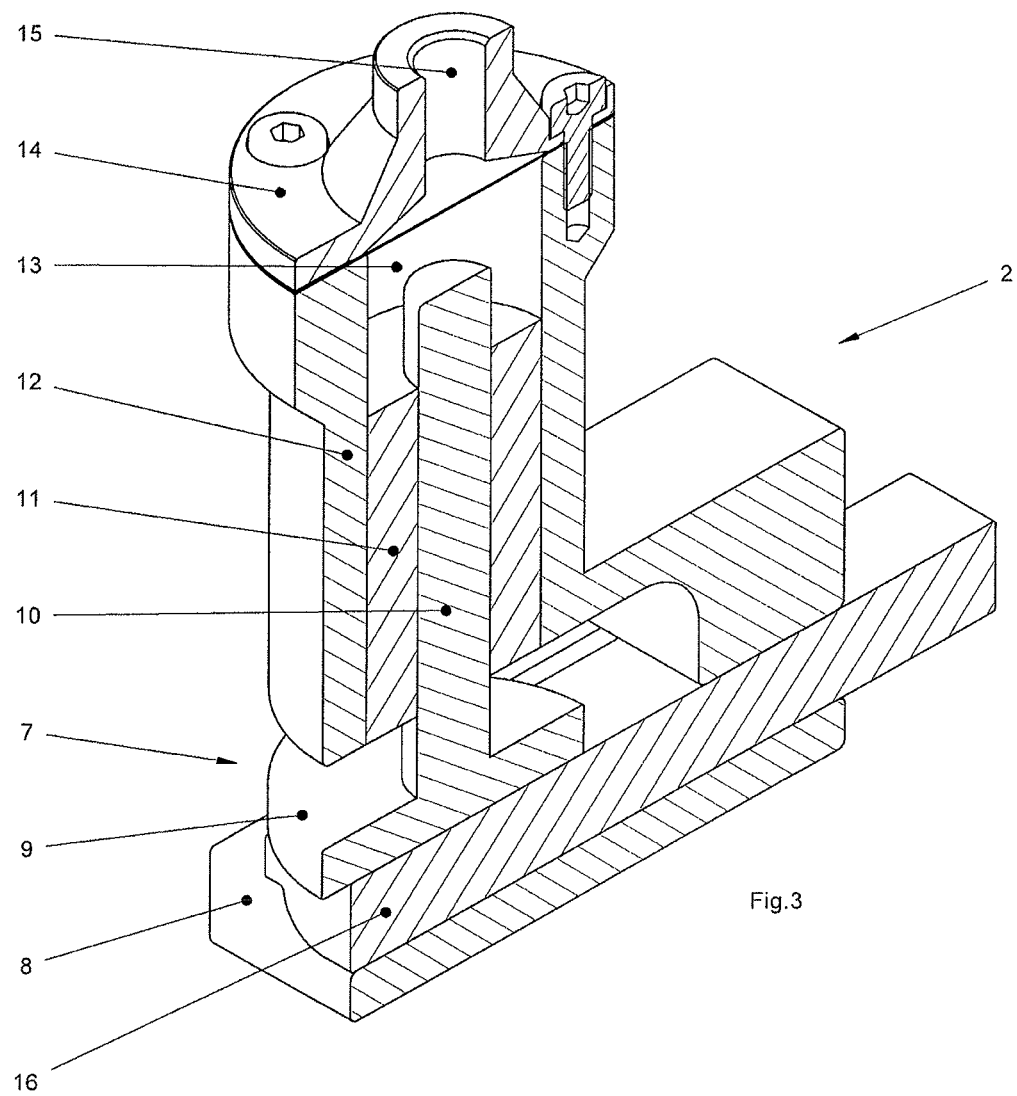
FIG. 3 is a view corresponding to that of FIG. 2 but wherein the measuring device is partially cut-away.
Figure 4:
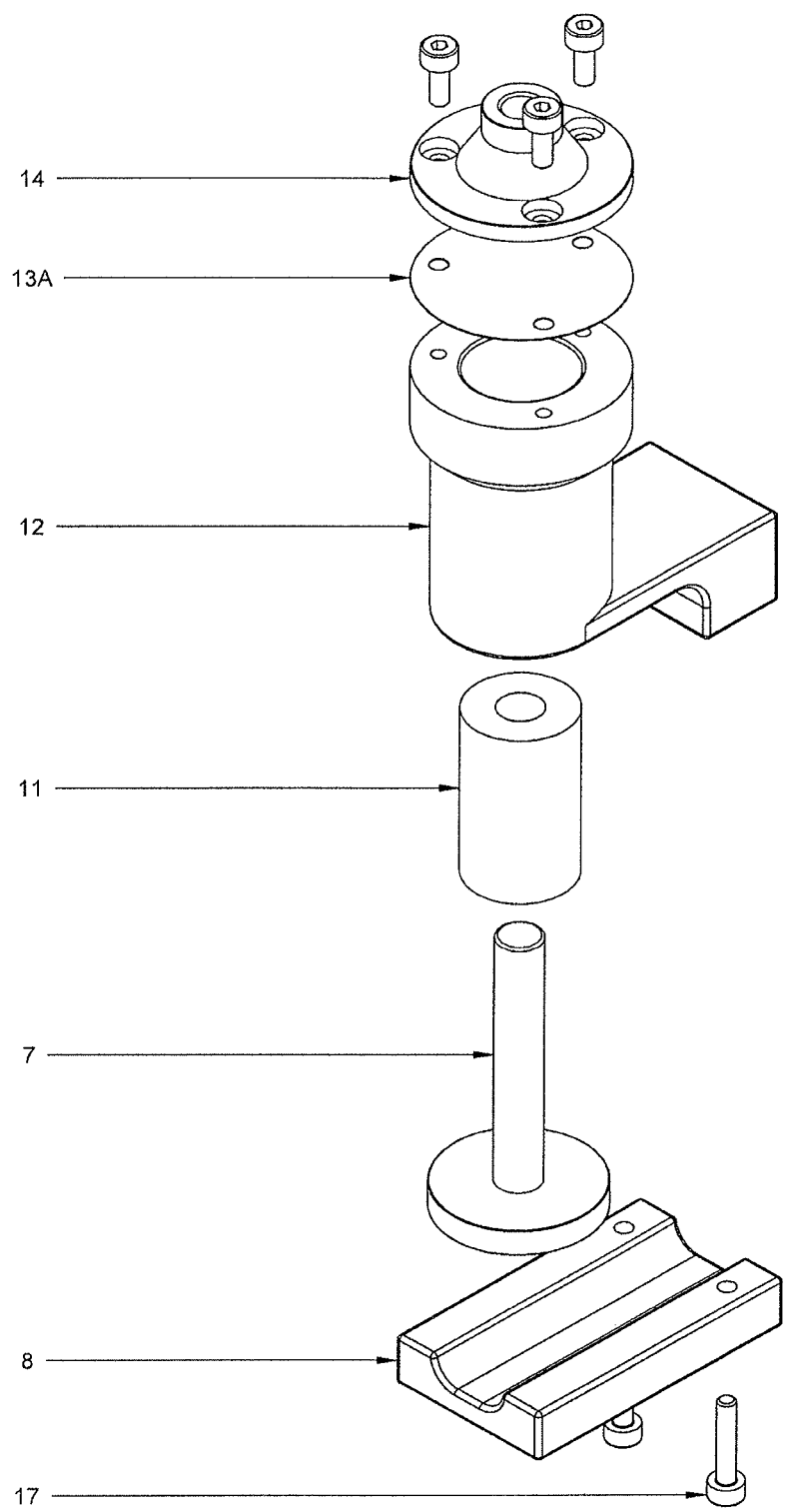
FIG. 4 is an exploded view of the measuring device of FIG. 2 without the perfusion sensor.

FIGS. 2-4 show an example of the first pressure measuring device 2 for measuring the local perfusion pressure in a body tissue. It includes a clamp for clamping the tissue so as to influence the perfusion in the tissue. The pressure exerted on the clamp is indicative for the perfusion pressure in the tissue.

The clamp of the measuring device 2 includes a first clamping member 7 and a second clamping member 8 (see FIG. 3). The first clamping member 7 comprises a pressure plate, in this case a circular pressure plate 9 attached to a plunger 10 slidable in a sleeve, such as a PTFE sleeve 11 fixedly incorporated in a cylinder 12. The cylinder includes a pressure room 13, that might be defined by a membrane 13A on one end (see FIG. 4) and is operatively connected to the plunger 10 (through the membrane which improves the fluid tightness of the pressure room 13) in order to exert pressure on the plunger 10 when the pressure in the pressure room 13 is above ambient pressure. A cover 14 of the pressure room 13 and cylinder 12 is provided with a connection 15 for the pressure line 4 to connect the pressure room 13 to the pump 3 which is able to pump fluid, such as air or another gas, into the pressure room 13 to pressurize it and increase pressure on the plunger and pressure plate of the first clamping member 7.

The second clamping member 8 is fixed to the cylinder 12 so that the first clamping member 7 can move with respect to the second clamping member 8. The second clamping member 8 includes a pressure surface which is here formed on a perfusion sensor 16. The perfusion sensor 16 is here clamped on the second clamping member by screws 17.

The perfusion sensor 16 is able to measure the perfusion in the tissue to be evaluated. The sensor 16 can operate on the basis of known techniques, such as Laser-Doppler Flowmetry (LDF) to measure flow, Near-Infrared Spectroscopy to measure oxygenation, pulsoxymetry, visual measurements by CCD, perfusion measurements using sensors measuring light scattering and/or absorption of light from one or more LED's or other light sources, comparable to pulsoxymetry etc. Because the sensor forms the clamping surface of the pressure measuring device, the perfusion is measured at the position where pressure is exerted on the tissue, so there is a direct relationship between the pressure on the tissue and perfusion in it. Perfusion could also be measured slightly downstream of the pressure surface because there the perfusion is also influenced by the pressure on the tissue.

The first pressure measuring device allows measuring perfusion pressure, such as the diastolic pressure or systolic pressure. Systolic pressure is measured when the perfusion is completely stopped which can be determined by the perfusion sensor 16. The pressure at reperfusion (when blood starts to flow again) can also be measured. The perfusion sensor and pressure measuring device can be used in combination to measure pressure that are most indicative for the tissue viability.

If for example bowel tissue should be evaluated, the bowel can be laid flat and the flat bowel can be clamped so that two tissue layers are clamped one onto the other. Tissue can then also be evaluated on a closed organ. However, it is also conceivable to only clamp one layer of tissue of an opened organ. Several measurements can be carried out around the circumference of the tissue to be evaluated. If two parts of tissue should be interconnected by anastomosis for example, both tissue parts to be connected should be evaluated as to their viability.

From the foregoing it will be clear that the invention provides a system and method for predicting the viability of a body tissue in a patient, which are simple and easy to use.

The invention is not limited to the embodiments shown in the drawings and described above, which may be varied in different ways within the scope of the appended claims. The local perfusion pressure measuring device may for example be adapted to the requirements of laparoscopic surgery.

The invention claimed is:

1. A method of performing surgery on tissue within a patient, the method comprising:
   accessing selected body tissue within a patient having viable and non-viable portions of tissue;
   utilizing a system to ascertain a first portion of viable tissue of the selected body tissue and a second portion of viable tissue of the selected body tissue, the first portion of viable tissue being spaced apart from the second portion of viable tissue wherein the non-viable portion of tissue is disposed between the first portion of viable tissue and the second portion of viable tissue, the system comprising a first pressure measuring device having a clamp configured to clamp a portion of the selected body tissue and configured to measure local perfusion pressure in the clamped portion of the selected body tissue, a second pressure measuring device configured to measure systemic perfusion pressure of the patient, and a feedback indicator configured to indicate viability of the clamped portion of the selected body tissue based on a ratio between the measured local and system perfusion pressures, wherein utilizing the system comprises ascertaining the non-viable portion to be removed from the first portion of viable tissue to the second portion of viable tissue by clamping the first pressure measuring device to different portions of the selected body tissue until the first portion of viable tissue and the second portion of viable tissue are ascertained based on if the feedback indicator indicates a clamped portion of the selected body tissue is non-viable or viable;
   removing the non-viable portion of tissue between the first portion of viable tissue and the second portion of viable tissue; and
   connecting the first portion of viable tissue to the second portion of viable tissue.

2. The method of claim 1, wherein the local perfusion pressure is measured simultaneously with measuring the systemic perfusion pressure.

3. The method of claim 2, wherein the local perfusion pressure is registered at a time local perfusion in the clamped portion of the selected body tissue stops or restarts.

4. The method of claim 1, wherein the local perfusion pressure is measured while clamping the clamped portion of the selected body tissue in the clamp and applying pressure with the clamp.

5. The method of claim 4, wherein a double layer of tissue is clamped in the clamp.

6. The method of claim 1, wherein the local perfusion pressure is measured through Laser Doppler measurements or pulsoxymetry.

7. The method of claim 1, wherein the systemic perfusion pressure is measured through an arterial line.

8. The method of claim 1, wherein the ratio is calculated by dividing the local perfusion pressure by the systemic perfusion pressure.

9. The method of claim 1, wherein connecting the first portion of viable tissue to the second portion of viable tissue is through anastomosis.

10. The method of claim 1 wherein the clamp comprises a clamp having two clamping members configured to clamp the tissue there between;
    a pressing unit configured to apply pressure on at least one of the clamping members;
    a pressure meter configured to measure a pressure applied by the pressing unit;
    a perfusion sensor configured to measure the local perfusion pressure in the tissue at or downstream of the clamp; and
    a cylinder-piston unit comprising a piston and a cylinder, wherein a first clamping member of the two clamping members is attached to the piston and a second clamping member of the two clamping members is attached to the cylinder.

11. The method of claim 10, wherein the perfusion sensor is positioned in one of the clamping members.

12. The method of claim 11, wherein the perfusion sensor forms at least a part of a clamping surface of one of the clamping members.

13. The method of claim 10, wherein the pressing unit is a pneumatic pressing unit including a pump.

14. The method of claim 13, wherein the pressure meter is a manometer.

15. The method of claim 14, wherein the manometer is integrated in the pump.

16. The method of claim 10, wherein removing the non-viable portion of tissue between the first portion of viable tissue and the second portion of viable tissue is based on determination of tissue viability by pulsoxymetry measurements.

17. The method of claim 1, wherein utilizing the system includes the system rendering colored light indicative of the viability of the clamped portion of the selected body tissue with the feedback indicator.

18. The method of claim 1, wherein utilizing the system includes the system outputting audible feedback indicative of the viability of the clamped portion of the selected body tissue with the feedback indicator.

19. The method of claim 1, wherein the local perfusion pressure is measured through Laser Doppler measurements.

20. The method of claim 1 wherein the ratio is an index.

21. A method of performing surgery on tissue within a patient, the method comprising:

providing a system comprising a computing device receiving signals from a first pressure measuring device and a second pressure measuring device;

accessing selected body tissue within a patient having viable and non-viable portion of tissue;

identifying the non-viable portion of tissue and identifying a viable portion of tissue attached to the non-viable portion of tissue, wherein identifying the non-viable portion of tissue and identifying a viable portion of tissue attached to the non-viable portion of tissue comprises:

measuring the local perfusion pressure in different portions of the selected body tissue of the patient with the first pressure measuring device;

measuring the systemic perfusion pressure of the patient with the second pressure measuring device;

using the computing device to calculate an index for each of the different portions based on the basis of the measured local perfusion pressure in each respective portion and the measured systemic perfusion pressure; and determining on the basis of the index which portion is the non-viable portion of tissue; and removing the non-viable portion of tissue.

22. The method of claim 21, wherein measuring the local perfusion pressure comprises clamping the tissue between two clamping members and measuring a thus applied clamping force while also measuring the perfusion in the tissue in relation to the applied clamping force.

23. The method of claim 21, wherein accessing the selected body tissue within the patient comprises performing open or laparoscopic surgery on the patient, and wherein measuring the local perfusion pressure in different portions of the selected body tissue comprises measuring the local perfusion pressure of body tissue within the patient during the open or laparoscopic surgery.

\* \* \* \* \*